United States Patent [19]

Okabe et al.

[11] Patent Number: 5,232,834
[45] Date of Patent: Aug. 3, 1993

[54] ANTI-HUMAN SPERM ANTIBODY, AND ITS PRODUCTION AND USE

[75] Inventors: Masaru Okabe; Tsutomu Mimura, both of Osaka, Japan

[73] Assignee: FUSO Pharmaceutical Industries, Ltd., Osaka, Japan

[21] Appl. No.: 493,279

[22] Filed: Mar. 14, 1990

[30] Foreign Application Priority Data

Mar. 15, 1989 [JP] Japan .................. 1-063300
Sep. 27, 1989 [JP] Japan .................. 1-251190

[51] Int. Cl.$^5$ .............. G01N 33/567; G01N 33/543; G01N 33/546; C08G 75/14
[52] U.S. Cl. .................... 435/7.21; 436/518; 436/533; 436/519; 436/811; 530/388.2; 435/7.2; 435/7.92; 435/7.93; 435/7.94; 435/806; 435/960; 435/70.21
[58] Field of Search .............. 435/7.2, 7.94, 7.95, 435/240.26, 806, 7.1, 960, 7.21, 7.92, 7.93, 806, 70.21; 530/387, 388.2; 436/503, 811, 518, 519, 533

[56] References Cited

FOREIGN PATENT DOCUMENTS 205293 12/1986 European Pat. Off. .

OTHER PUBLICATIONS

Saling et al (1986) Abstract of Adv Exp Med Biol 207:95-111.
Okabe et al (1986) Abstract of J Reprod Immunol 9:67-70.
Kawai et al (1989) Abstract of J Reprod Immunol 16:71-82.
Kohler et al (1975) Nature 256:495-497.
Isahakia et al (1984) Abstract of Biol Reprod 30:1015-1026.
Kallajoki et al (1984) Abstract of Int J Androl 7:283-296.
Primakoff et al (1985) Abstract of J Cell Biol 101:2239-2244.
Lee et al (1985) Abstract of J. Reprod Immunol 7:3-14.
Kamada et al (1985) Am J Obst & Gyn 153:328-331.
Wolf et al (1985) Abstract of Biol Reprod 32:1157-1162.
Saling (1986) Develop Biol 117:511-519.
Ochs et al (1986) Exp Cell Res 167:495-504.
Wolf, D. P, et al, Biological Abstracts, vol. 81, No. 5, Abstract No 47912 (1986).
Kallajoki, M., et al, vol. 79, No. 5, Abstract No. 44868 (1985).
Symposium on Fertilization in Mammals, Final Program and Abstract Book, Aug. 1 to 5, 1989, Newton, Mass., p. 60, II-20.
Okabe, M., et al, Journal of Reproductive Immunology, 9, pp. 67-70 (1986).
Okabe, M., et al, Journal of Reproductive Immunology, 13, pp. 211-219 (1988).
Okabe, M., et al, Nihon Funin Gakkai Zassi (Annual Report of Japan Sterility Society), 33, No. 3, 473-478 (1988).
Okabe, M., et al, J. Pharmacobio-Dyn., 9, 55-60, (1986).

*Primary Examiner*—Christine M. Nucker
*Assistant Examiner*—D. R. Preston

[57] ABSTRACT

A monoclonal or polyclonal antibody having a specific binding property to an antigenic site on the human sperm acrosome, which is produced by a hybridoma obtained by fusion between an antibody-producing mammalian (except human) cell immunized with the antigenic site on the human sperm acrosome and a cell having permanent proliferation potency.

4 Claims, No Drawings

ANTI-HUMAN SPERM ANTIBODY, AND ITS PRODUCTION AND USE

The present invention relates to an anti-human sperm antibody, and its production and use. More particularly, it relates to an anti-human sperm antibody, a process for producing said antibody and a reagent for evaluation of the fertilizability of sperm using said antibody. It also relates to a hybridoma producing said antibody and a method for obtaining said hybridoma.

The term "fertilizability" as herein used indicates an ability that sperm penetrate into zona pellucida and fuse with ova.

It is known that mammalian sperm have no fertilizability in an ejaculated state and, as the result of an acrosome reaction in a female uterus, gain fertilizability through the change of physiological function. In the acrosome reaction, fusion takes place between the cell membrane at the acrosomal portion and the outer acrosomal membrane to release acrosomal enzymes. Simultaneously, both of said membranes are separated from the sperm body to reveal the inner acrosomal membrane. It is also known that ejaculated sperm can gain fertilizability when incubated.

Conventionally, determination of the fertilizability aiming at the diagnosis or therapy of sterility has been made through measurement of the amount, concentration, motility, etc. of sperm. However, this determination is not reliable, because it does not comprise the direct observation of the fertilizability. In recent years, there is developed a method for testing whether fusion takes place between incubated sperm and hamster ova (being capable of fusing with human sperm) (i.e. the hamster test), but this method is complicated in operation and not good in reproducibility. There is also developed a method comprising various staining steps in combination (i.e., the triple staining), but this method is again complicated and not sufficiently reliable.

Accordingly, it has been a long demand to establish a convenient, reproducible and reliable method for evaluation of human sperm fertilizability.

As the result of an extensive study, the present inventors have succeeded in producing a monoclonal or polyclonal antibody specific to the antigenic site appearing on a fertilizability-acquired human sperm. They also succeeded in staining specifically fertilizability-acquired human sperm by the use of said antibody according to the labeled antibody technique (e.g. fluorescent or enzymo-antibody technique). Based on these successes, the diagnosis of male sterility can now been made easily and rapidly with high reliability.

A main object of the present invention is to provide an antibody, particularly a monoclonal antibody, having a specific binding property to an antigenic site of the human sperm acrosome. The term "human sperm acrosome" in this specification covers not only an outer acrosomal membrane but also an inner acrosomal membrane, unless otherwise stated.

Another object of this invention is to provide a hybridoma capable of producing said antibody, obtained by fusion between an antibody-producing mammalian (except human) cell immunized with the antigenic site on the human sperm acrosome and a cell having permanent proliferation potency.

Another object of the invention is to provide a reagent for evaluation of a human sperm fertilizability, which comprises said antibody as labeled or non-labeled and, in case of said antibody being non-labeled, additionally a labeled second antibody.

A further object of the invention is to provide a process for producing said antibody by culturing said hybridoma and recovering the produced antibody from the resultant culture.

A further object of the invention is to provide a method for obtaining said hybridoma, which comprises fusing antibody-producing mammalian (except human) cells immunized with the antigenic site of the human sperm acrosome with cells having permanent proliferation potency and selecting hybridomas capable of producing an antibody having a specific binding property to an antigenic site of the human sperm acrosome from the fused cells.

A still further object of the invention is to provide test beads for evaluation of the fertilizability of a human sperm, which comprises solid beads and an antibody bound onto their surfaces, said antibody being specific to an antigenic site on the human sperm acrosome.

A still further object of the invention is to provide a kit for evaluation of the fertilizability of a human sperm, which comprises (a) said test beads or (a') solid beads and an antibody being capable of binding to their surfaces, (b) a magnet and (c) a culture medium for sperm incubation, said antibody being specific to an antigenic site on the human sperm acrosome.

These and other objects of the invention will be apparent to those skilled in the art from the foregoing and subsequent descriptions.

PREPARATION OF THE ANTIBODY

1. Immunization

The antibody according to the invention is obtainable through immunization of a mammalian animal with the antigenic site on the human sperm acrosome. The human sperm revealed at the acrosome (hereinafter referred to as "capacitated human sperm") can be obtained, for instance, by pre-incubating the ejaculated sperm in a medium containing human serum albumin or treating the ejaculated sperm with an anionic surfactant (e.g. sodium deoxycholate), a cationic surfactant, a non-ionic surfactant or an amphoinic surfactant, or with an ionophore (e.g. A23187). For immunization, a mammalian animal such as mouse or rat is treated with the capacitated human sperm intraperitoneally, intravenously, subcutaneously or the like. The mammalian animal is preferred to be of the same species as that, from which the cells having permanent proliferation potency for cell fusion are obtained. The age of the animal is not limitative and may be, for instance, about 5 to 10 weeks old in case of mouse. No sexual limitation is present on the animal. The amount of the capacitated human sperm to be used for immunization may be, for instance, from about $5 \times 10^6$ to $2 \times 10^7$ per mouse. On the treatment, the capacitated human sperm is preferably used in the form of a suspension or emulsion in phosphate-buffered saline (PBS) or mixed with Freund's Complete Adjuvant (FCA). The treatment may be effected 1 to 5 times with intervals of 1 to 3 weeks. The final immunization is performed by intravenous or intraperitoneal administration of a suspension of the capacitated human sperm in PBS to the animal. From the body fluid or antibody-producing cells of the thus immunized animal, a polyclonal antibody can be obtained, and the collection of such body fluid or antibody-producing cells may be made after confirmation of the rise of the antibody titer up to a sufficiently high level.

2. Cell fusion

As stated above, the antibody-producing cells are obtainable from the animal immunized with the capacitated human sperm. Obtainment of those cells may be made from a spleen, lymphocytes, peripheral bloods, etc. of the animal, among which the spleen is the most preferred. For example, the spleen is aseptically taken out 2 to 5 days after the final immunization and chopped to make a suspension of spleen cells in Dulbecco's Modification of Eagle's Medium (MEM), followed by centrifugation to collect the spleen cells.

As the permanent proliferating cells for cell fusion, there may be used any cells having permanent proliferation potency, and the most commonly used are myeloma cells, particularly from the animal of the same species as that, from which the antibody-producing cells are obtained. In case of mouse, for instance, the permanent proliferating cells such as P3U1P3X63-Ag8.U1 (P3U1), P3/NS1/1-Ag4-1 (NS-1), SP2/0-Ag14 (SP2), P3X63Ag8 (X63), P3X63-Ag8.653 (653), etc. are employed. Particularly preferred are those having a characteristics serving as a marker on selection, and their representative examples are 8-azaguanine-resistant mutant, hypoxanthine-guanine phosphoribosyl transferase (HGPRT) deficient mutant, etc. These cells are commercially available, for instance, from American Type Culture Collection (ATCC), Fujisawa Pharmaceutical Co., Ltd., Dai-Nippon Pharmacuetical Co., Ltd., etc. Prior to cell fusion, these cells are cultured in a proliferative culture, washed with Dulbecco's MEM and collected by centrifugation.

Cell fusion may be, for instance, carried out as set forth below. Antibody-producing cells (e.g. spleen cells) and permanent proliferating cells (e.g. myeloma cells) are mixed together in a cell proportion of 2 to 10:1. To the cell mixture kept at 37° C., a fusion promoter such as polyethylene glycol (PEG, average molecular weight=1300-7500, 20-40%) is gradually added thereto to initiate the fusion. Alternatively, the cell mixture may be electrically sensitized under such a high direct voltage as about 1000 V/cm for a short time so that the cell fusion takes place. After addition of a culture medium to stop the fusion, the resulting mixture is subjected to centrifugation. The collected cells are suspended in a hypoxanthine-aminopterin-thymidine-containing proliferative medium (HAT medium), and the cell suspension is inoculated in a 96 well microplate at a rate of 200 $\mu$l/well and cultured in a $CO_2$ incubator (37° C., 5% $CO_2$, 95% humidity; the culture conditions in the $CO_2$ incubator as hereinafter referred to being the same as above) for about 1 week, during which the culture medium is replaced by a HAT medium every half amount at intervals of 2 days. Finally, replacement is made by the use of a hypoxanthine-thymidine-containing proliferative medium (HT medium) instead of a HAT medium.

3. Screening and cloning of the hybridoma

Cultivation in the HT medium is continued for several days. When the proliferative colony, i.e. hybridomas, grows to half the well, the hybridomas in each well are subjected to screening to check their productivity of a human sperm-specific monoclonal antibody. Screening may be carried out, for instance, by taking a portion of the supernatant in the well where hybrodomas grow and examining its reactivity to human sperm by a per se conventional technique such as enzyme-labeled antibody technique or fluorescent antibody technique.

Thereafter, by a per se conventional technique such as the limiting dilution method or the agarose method, cloning of the hybridomas being capable of producing a human sperm specific monoclonal antibody is effected to establish a large number of hybridomas which can produce a single monoclonal antibody. Cloning as well as screening may preferably be carried out at least more than two times for accuracy.

4. Production of the monoclonal antibody

The thus established hybridomas are subjected to in vitro (e.g. in a culture tube or a nutrient medium) or in vivo (e.g. in a living body or an animal tissue) cultivation to produce a monoclonal antibody. The in vitro cultivation is, for example, carried out in a proliferative medium by the use of a $CO_2$ incubator. When the hybridomas grow to their maximum proliferative point, the culture medium is collected and centrifuged to separate the cell bodies and the supernatant. The monoclonal antibody in the supernatant may be used as such or separated, for instance, by treatment with ammonium sulfate to salt out, dialysis with 0.02M phosphate buffer (pH, 7.2) and passing through a diethylaminoethyl cellulose column for purification.

The cell bodies (i.e. hybridomas) separated from the supernatant are suspended in a suitable medium such as Dalbecco's MEM added with dimethylsulfoxide (5-10% (v/v)) and bovine fetal serum (10-20% (v/v)) to make a cell concentration of $1-10 \times 10^6$ cell/ml. The suspension was admitted into sterilized vials and gradually freeze-dried below $-80°$ C. The hybridomas can be thus stored in the living state over a long period of time. It is also possible to preserve the hybridomas almost eternally when they are stored in such an extremely cold state as in liquid nitrogen.

The in vivo cultivation of the hybridomas may be effected by inoculating them into an appropriate animal, preferably the animal of the same species as that, from which the spleen cells for fusion are taken out. In case of using a BALB/c mouse, for instance, 2,6,10,14-tetramethylpentadecane (pristane) (0.5 ml) is intraperitoneally injected to the animal one to three weeks before the inoculation, and then the hybridomas were intraperitoneally given to said animal in an amount of $2-10 \times 10^6$ cells/mouse. After one to two weeks, an ascitic fluid containing the monoclonal antibody in a high concentration is produced in the abdomen of the animal. The ascitic fluid is collected and purified in the same manner as in the case for the supernatant.

5. Characteristics of the monoclonal antibody

The monoclonal antibody thus obtained is subjected to determination of its characteristics, i.e. the reactivity to the antigenic site on the human sperm acrosome, by a per se known antibody-labeled technique such as fluorescent antibody technique or enzyme-antibody technique. Thereafter, the specificity of the monoclonal antibody is confirmed by the per se known labeled immune determination method (e.g. enzymoimmune determination method) through investigation of the reactivity to human seminal plasma or mouse sperm.

As explained above, the antibody according to the invention is usable for diagnosis or therapy of male sterility by detecting the human sperm fertilizability. Specifically, the detection may be performed by contacting a human sperm to be tested with the labeled antibody of the invention and detecting the labeling attached to the sperm by any conventional detecting means. Alternatively, a human sperm is first contacted with the non-labeled antibody of the invention and further contacted with a labeled second antibody which can be bound to said antibody of the invention, followed by detection of the labeling attached to the sperm by any conventional detecting means.

For the labeling of the antibody, there may be employed radioactivity, enzymes, fluorescent compounds (e.g. fluorescein isothiocyanate, tetramethyl rhodamine isothiocyanate), etc. Preparation of the second antibody and its labeling are achieved by a per se conventional procedure.

For the detection as stated above, it is convenient to use a diagnozing kit comprising a labeled or non-labeled antibody having a specific binding property to an antigenic site on the human sperm acrosome according to the invention and, in case of said antibody being non-labeled, a labeled second antibody, optionally with any other reagent and/or apparatus (e.g. sperm collector, buffer solution, chamber slide).

A typical example of the convenient procedures for the detection will be explained below.

PREPARATION OF THE TEST BEADS

The test beads usable in this invention are obtainable by binding suitable solid particles (e.g. chromatogel) physically or chemically with the antibody of the invention. Preferably, however, the solid particles are first bound chemically with an antibody specific to the antibody of the invention (i.e. second antibody), protein A, protein G, etc. and then bound with the antibody of the invention due to its specific binding to the second antibody.

As the solid particles, there may be used any solid beads made of glass, agarose, Sepharose ®, porous diatomaceous earth filled with Sepharose ®, hydrophilic copolymerized acrylic gel, polystyrene, etc. Preferably, the beads have a ultra constant magnetic property by incorporating a magnetic element (e.g. $Fe_2O_3$) in the core. The solid beads may be in any shape but is preferred to be in spheres. The particle size is not restricted but may be usually from several to several hundred micrometers.

Chemical binding of the second antibody, protein A, protein G, etc. to the solid beads is preferably performed after activation of the solid beads. The activation is accomplished by a per se conventional procedure for binding a protein to solid beads of this kinds. Representative examples of such procedure is the ones using tosyl chloride, cyanogen bromide, acetyl bromide, glutaraldehyde or the like. Some of these activated solid beads are commercially available on the market. Said activation as well as binding of a protein such as the second antibody, protein A or protein B onto the activated solid beads may be carried out by a per se conventional procedure. Examples of the commercial solid beads bound with the second antibody, protein A, protein B or the like are "Dynabeads ® M-450" and "Dynabeads ® M-280" respectively coated with sheep anti-mouse IgG, goat anti-mouse IgG, sheep anti-rat IgG or sheep anti-rabbit IgG (Nihon Dynacel Inc.), goat anti-mouse IgG(H&L) carboxylate beads, goat anti-rabbit IgG(H&L) carboxylate beads, protein A carboxylate beads, goat anti-rabbit IgG(H&L) micromagnet particles, protein A micromagnet particles and sheep anti-mouse IgG(H&L) micromagnet particle (Polyscience Inc.), etc.

Binding of the antibody of the invention onto the solid beads as above may be performed by treating a suspension of the solid beads in a suitable medium (e.g. buffer) with a proteinic solution to eliminate non-specific adsorption and mixing the treated solid beads with an ascitic fluid containing the antibody or a solution containing the antibody as purified.

Test method:

From a male human person to be examined, the sperm is collected, a sperm suspesnion is made therewith. Immediately after the collection and 24 hours after the incubation, the sperm suspension is admixed with the test beads prepared as above, and incubation is continued for a period of 10 to 30 minutes. The test beads are separated from the suspension, washed and subjected to measurement of the number of sperm bound to the solid beads per 100 particles, for instance, by the aid of a microscope. Centrifugation should not be applied on sepration and washing of the test beads as the sperm are apt to release from them. The capacitated sperm revealing their antigenic side on the acrosome bind to the solid beads in ratios of 1:1, 1:2, 2:1, 1:3, 3:1, 2:3, 3:2, etc. The fertilizability may be determined as good when the binding ratio is not more than 5 immediately after the collection and not less than 25 after 24 hours' incubation.

Preparation of the diagnosing kit:

For facilitating the evaluation, it is convenient to make a kit comprising the test beads, a magnet and a medium for sperm incubation. The medium for serum incubation may comprise inorganic salts, organic salts, sugars, serum albumin, antibiotics, indicators, etc. Additionally, the kit may comprise a test tube, a tube for centrifugation or any other glass-made container analogous thereto, a pipette or any other suction instrument analogous thereto, a microscope and the like. Instead of the test beads, there may be used the combination of the solid beads and the antibody.

Effect:

According to the invention, sperm are contacted onto the antibody-bound test beads, and the number of sperm bound onto said beads is counted, whereby the fertilizability is evaluated. Thus, the fertilizability can be easily evaluated in a short time without troublesome measurement of radioactivity, fluoresense or the like. Since counting can be effected directly under a microscope, the outcome is quite reliable. Accordingly, this invention will make the rapid and objective diagnosis of sterility possible.

Practical and presently preferred embodiments of the invention will be explained in detail in the following Examples.

EXAMPLE 1

Preparation of anti-human sperm monoclonal antibody:

For evaluation of the fertilizability, it is necessary to obtain a monoclonal antibody reactive to an antigen appearing only in fertilizability-acquired sperm. Sperm generally commence an acrosome reaction prior to its fusion with ova, whereby the inner acrosomal membrane (hereinafter referred to as "IAM") is revealed. Thus, an antibody capable of detecting an antigen specific to IAM can react to the sperm surface with expression of the fertilizability. Said antigen has a high possibility of participation in co-recognition between sperm and ova. Accordingly, sperm were treated under various conditions so as to make their IAM highly revealed and used for immunization.

Preparation of sperm suspension

As the medium, there was used a modified Biggers-Whitten-Whittingham medium (hereinafter referred to as "m-BWW") containing 0.3% human serum albumin (hereinafter referred to as "HSA") (Fraction V powder; Sigma Chem.) according to the Kamiguchi et al. method.

Human adult male sperm were liquefied with air containing 5% $CO_2$ at 37° C. for 30 to 60 minutes, 0.5 ml each of the liquefied sperm was admitted in a small test tube, and m-BWW (2 ml) was layered thereon. In order to increase the contact area with the liquefied sperm, the test tube was inclined at an angle of 30°, and then said tube was sealed with a parafilm and incubated in air containing 5% $CO_2$ at 37° C. for 60 minutes. The supernatant was collected by a micropipette ("Pipetman p-1000" ®; Gilson), and the sperm therein were washed with m-BWW two times. The sperm thus washed were admixed with m-BWW (HSA concentration, 3.5%) (1 ml) to make a sperm suspension, which was subjected to A23187 treatment for capacitation or IAM reveal.

A23187 treatment

It is electroscopically observed that the sperm treated with A23187 cause the acrosome reaction in a higher rate. Thus, the sperm suspension obtained above was treated with A23187 (free acid; Sigma Chem.) in a concentration of 10 μm for 10 minutes according to the Kamiguchi et al. method, washed with m-BWW two times and used for immunization.

Immunization to mouse

The sperm ($1 \times 10^7$ for each immunization) as treated above were immunized to C57BL/6 mouse. Immunization was effected by injection of the sperm to the animal on the 1st, 21st and 28th days and thereafter every 2 weeks until the rise of the antibody titer. On the injection, the sperm were emulsified with Freund's complete adjuvant for the first administration, emulsified with Freund's incomplete adjuvant for the second administration and suspended in PBS for the third and subsequent administrations. On the second and subsequent administrations, the serum was taken from the eyeground on the third day after each administration, and its antibody titer was measured by the indirect fluorescent antibody technique as hereinafter explained. When the sufficient rise of the antibody titer was confirmed, the spleen was taken out on the third day after the final administration, and the spleen cells were used for cell fusion.

Cell fusion and cloning

Cell fusion and cloning were carried out by a per se conventional procedure. Namely, hybridomas were prepared by fusing the spleen cells as obtained above with P3U1 mouse myeloma cell lines (Fujisawa Pharm.) in polyethylene glycol "PEG 4000" ® (molecular weight, 4000; Nakarai K.K.) and subjected to screening for obtaining those producing the antibody reactive to the human sperm. Screened positive cells were subjected to cloning by the limiting dilution method to establish a monoclonal antibody producing cell line, which was designated as "hybridoma MH61" and deposited according to the Budapest Treaty on Jan. 24, 1989 under accession number FERM BP-2257 at the Fermentation Research Institute, Agency of Industrial Science and Technology, located at Tsukuba-shi, Ibaragi-ken, Japan.

Staining by indirect fluorescent antibody technique

Screening of the antibody and measurement of the antibody titer were performed by the indirect fluorescent antibody technique. Namely, 50 μl of a sperm suspension ($1 \times 10^6$ sperm/ml) was diluted with 50 μl of a 20 fold PBS dilution of the supernatant or antiserum, and the resultant mixture was allowed to react at room temperature for 2 hours. The resulting mixture was washed with PBS two times, admixed with 10 μl of a 125 fold PBS dilution of FITC labeled goat anti-mouse Ig(A+M+G) (Cappel Inc.) containing 5% new born calf serum (hereinafter referree to as "NBCS") as the second antibody and reacted at room temperature for 1 hour. The reaction mixture was washed with PBS two times and subjected to observation by a fluorescence microscope.

In vivo proliferation of antibody producing cells

Hybridomas MH61 collected in the logarithmic growth phase were injected to CBF1 (Balb/csC57BL/6) male mice, as pretreated (10 to 20 days before) with 0.5 ml of "Pristane" ® (p-1403; Sigma Chem.), at a rate of $1$–$2 \times 10^7$ cells/mouse. In about two weeks, proliferation of cells as the ascités tumor could be observed. When the body weight of each mouse increased more than 40 g, the ascitic fluid was collected, freeze-dried at −80° C. and kept under liquid nitrogen.

EXAMPLE 2

Detection of antigen-determining site to which anti-human sperm monoclonal antibody specifically binds:

(1) Cross reaction

The components in seminal plasma firmly attach to sperm as ejaculated and are hardly removable by ordinary washings. They have a strong antigenicity so that the antibody to seminal plasma may be produced on the immunization of the sperm. The antibody which this invention aims at is the one which can detect the sperm membrane changes during capacitation and should remain unreactive to seminal plasma.

Preparation of human seminal plasma

The seminal fluid of male adult was allowed to stand in 5% $CO_2$ containing air at 37° C. for 30 to 60 minutes. To the thus liquefied sperm, an equivalent amount of m-BWW was added. The mixture was centrifuged at 1500 xg for 5 minutes to remove sperm. The supernatant was again centrifuged for complete removal of sperm to obtain a seminal plasma.

Study on reactivity of seminal plasma and antibody

The reactivity of the antibody to the seminal plasma was measured by the enzyme-linked immunosorbent assay method (ELISA). As the positive and negative controls, there were used respectively a glutaraldehyde-immobilized human sperm (Wako Pure Chemical K.K.) and a m-BWW solution.

50 μl of the seminal fluid containing the antigen was placed on the ELISA microplate "Farcon #3911" ® and dried at 37° C. overnight for adsorption of the antigen thereon, followed by washing with a tris-buffered sodium chloride solution containing 0.05% Tween 20 TM (Nakarai K.K.) (pH, 7.4; hereinafter referred to as "Tween-TBS") three times. 200 μl of PBS containing 5% skim milk (Morinaga Skim Milk K.K.) was admitted therein, and the resultant adsorbed antigen was allowed to stand at room temperature for 1 hour for blocking.

The antigen was washed with Tween-TBS three times, and 50 μl of a 1000 fold dilution of the ascitic fluid with 1% BSA-PBS was added thereto as the antibody, followed by reaction for 2 hours. After washing, 50 μl of a 1000 fold dilution of peroxidase-labeled goat anti-mouse Ig(A+M+G) (Cappel Inc.) with 1% BSA-PBS was added thereto, followed by reaction at room temperature for 2 hours. After washing, the reactivity of the antibody was observed by coloration with a substrate. Thus, 100 μl of a substrate solution comprising a 0.1M citric acid-buffer solution (pH, 4.5) containing o-phenylenediamine (0.1%; Nakarai K.K.) and hydrogen peroxide (1.2%) were added to the plate, the reaction was carried out for 30 minutes while prevention of light. The coloration was stopped by addition of 12.5% sulfuric acid (50 μl), and the absorbance at 450 nm was measured. The antibody MH61 did not show any reactivity to human seminal plasma.

(2) Assay on reactivity variation of antibody to artificially capacitated sperm

For evaluation of the sperm fertilizability with the antibody, it is necessary that the antibody recognizes the antigenic determinant of the sperm appearing with capacitation. Whether the sperm is capacitated or not can not be surely proved unless the sperm is really fused with human egg. However, Green et al reported on the basis of the electroscopic observation that when treated with an ionophore A23187, the number of sperm which have caused the acrosome reaction is increased. Accordingly, study was made to determine whether any difference in reactivity can be detected between fresh sperm and the sperm treated with A23187.

Test method

Preparation of human sperm suspension

Human sperm suspension was prepared in the same manner as in Example 1, and A23187 was added thereto to make a final concentration of 10 μM, followed by reaction for 10 minutes. The reaction mixture was centrifuged at 500xg to remove A23187 and washed with m-BWW two times to obtain a A23187-treated sperm.

Observation on reactivity to antibody

The sperm was stained by the indirect fluorescent antibody method and subjected to ovservation by a fluorescence microscope to ascertain the stained pattern of the sperm as well as its existing rate. The results are shown in Table 1.

TABLE 1

| Antibody | Localization (%) | | | | | | | | | | | | | | |
|---|---|---|---|---|---|---|---|---|---|---|---|---|---|---|---|
| | Ejaculated and washed | | | | | | | A23187 treated | | | | | | | |
| | W | T | H | A | M | AT | N | W | T | H | A | E | M | P | TE | AT | N |
| DE | 98 | 2 | — | — | — | — | — | 90 | 8 | — | — | — | — | — | 2 | — | — |
| MH61 | — | — | 3 | 1 | — | — | 96 | 11 | — | 45 | 22 | — | 2 | 1 | — | 2 | 13 |

*) W, whole body; T, tail; H, head; A, acrosome; E, equatorial segment; M, middle piece; P, posterior region; N, no staining.

It is understood from the above results that the antibody MH61 extensively reacts to the A23187 treated sperm but hardly does to the ejaculated and washed sperm. Further, the bound locus was limited to the acrosomal and head portions of sperm. These results are quite similar to those as observed with respect to OBF13, which is the antigen specific to the capacitated mouse sperm. If the antigenic determinant recognized by the antibody MH61 is a substance participating in the fertilization, then fertilization shall be prevented by addition of the antibody. The influence of the antibody MH61 on the sperm function was thus studied in the following example.

EXAMPLE 3

Influence of the antibody MH61 on the sperm function:

(1) Sperm aggregating activity

Some antibodies have a strong sperm aggregating activity. When many sperm aggregates due to such activity, the apparent sperm concentration lowers, and the fertilization is prevented.

Test method

Preparation of human sperm suspension

A human sperm suspension was prepared in the same manner as in Example 1, treated with A23187 (10 μM) for 10 minutes and then subjected to test.

Observation on sperm aggregation by antibody

The aggregating activity was measured by the microtiter method. Namely, a 500 fold dilution of an ascitic fluid as the antibody with 1% BSA (Fraction V powder; Simga Chem)-containing PBS (BSA-PBS) was charged in a microwell plate for blood aggregation reaction and diluted with BSA-PBS by 2 fold serial dilution. Each dilusion (50 μl) was combined with 50 μl of the human sperm suspension (1 × 10$^6$ cells/ml) as prepared above to make a 2 fold dilution and allowed to react in 5% $CO_2$-containing air at 37° C. for 1 hour. Sperm aggregation on the plate was observed by a phase-contrast microscope (x160). As the negative control, there was used an ascitic fluid containing P3U1 mouse myeloma cells diluted as above. The results are shown in Table 2.

TABLE 2

| Ascitic fluid | Dilution | | | | | |
|---|---|---|---|---|---|---|
| | 1000 | 2000 | 4000 | 8000 | 16000 | 32000 |
| P3U1 | — | — | — | — | — | — |
| YP | +++ | +++ | +++ | +++ | ++ | ++ |
| MH61 | — | — | — | — | — | — |

The anti-human sperm antibody YP used as the positive control exerted a strong sperm aggregating activity, whereas MH61 and P3U1 as the negative control showed no sperm aggregating activity.

(2) Influence of antibody on fusion and binding of sperm in hamster test.

Test method

Incubation was carried out according to the Kamiguchi et al method using 3.5% HSA-containing m-BWW. For preparation of sperm and ova, m-BWW containing 0.3% HSA was used.

The procedure for hamster test is shown below.

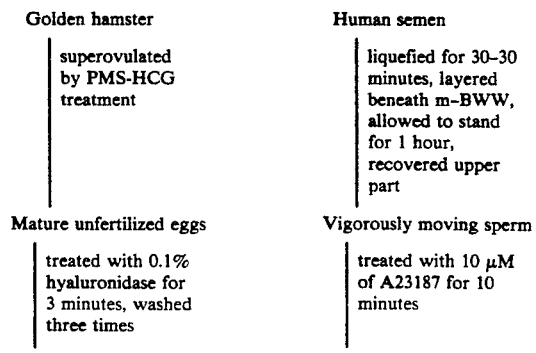

Golden hamster
  superovulated by PMS-HCG treatment

Mature unfertilized eggs
  treated with 0.1% hyaluronidase for 3 minutes, washed three times Human semen
  liquefied for 30–30 minutes, layered beneath m-BWW, allowed to stand for 1 hour, recovered upper part Vigorously moving sperm
  treated with 10 μM of A23187 for 10 minutes

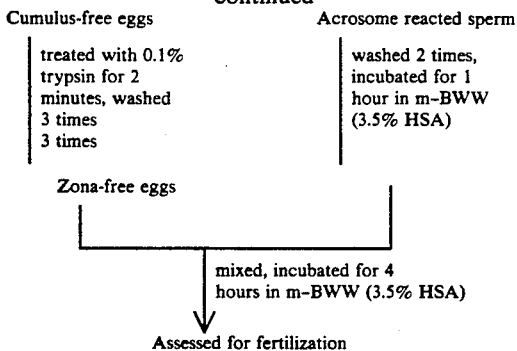

Preparation of human sperm suspension

In the same manner as above, a human sperm suspension was prepared. Prior to the insemination to ova, the human sperm suspension was pre-incubated in 5% $CO_2$-containing air at 37° C. for 1 hour.

Preparation of hamster ova

Preparation was carried out according to the Yanagimachi et al method. Namely, a juvenile female golden hamster was injected with PMS (30 i.u.; Teikoku Zoki) and, on 48 hours thereafter, with HCG (30 i.u.; Teikoku Zoki). Seventeen hours thereafter, the animal was sacrificed by deblodding, the abdomen was opened, and the oviduct was taken out. The oviduct was placed on a dish charged with m-BWW, its enlarged portion was broken by the aid of a needle under the observation with a steroscopic microscope ($\times 20$), and the ovum in cumulus clots was taken out, followed by washing. The ovum was treated with 0.1% hyarulonidase (Sigma, Type 1-S) for 3 minutes to make a cumulus-free epithelium, which was then washed with m-BWW three times and treated with 0.1% trypsin (Sigma, Type III) for 2 minutes to make zona-free. The resultant epithelium was washed with m-BWW three times and subjected to test.

Hamster test

A m-BWW solution (HSA concentration, 3.5%) containing 10 to 15 ova was diluted with an ascitic fluid as the antibody to make a 1000 fold dilution. Sperm were added thereto to make a final concentration of $1 \times 10^6$ cells/ml, and the solution volume was adjusted to 0.4 ml. After 4 hours, the ova were taken out and subjected to observation with a phase contrast microscope ($\times 320$). As the negative control, there was used an ascitic fluid of P3U1 mouse myeloma cells.

Test results

The results are shown in Table 3.

between the reactivity to ejaculated sperm and the reactivity to A23187-treated sperm. In view of the object of the invention, the antibody is desirable not only to control significantly the fertilization but also produce a significant difference between the reactivity to ejaculated sperm and the reactivity to A-23187-treated sperm. Therefore, further detailed study was made on the antibody MH61.

EXAMPLE 4

Reaction mode of human sperm with monoclonal antibody:

Since the proposal of hamster test by Yanagimachi et al, the study on its relationship with the actual sperm fertilizability was made. For instance, as the result of the observation with a phase contrast microscope, Tulbot et al reported that the acrosome reaction took place on all the human sperm attached to a hamster ovum. Based on this fact, the sperm on a hamster ovum were stained by the indirect fluorescent antibody method, and the reactivity to sperm undertaking the acrosome reaction was studied.

Test method

Preparation of human sperm suspension

The preparation was made according to the Mori et al method. Namely, human sperm was liquefied in 5% $CO_2$-containing air at 37° C. Into a small test tube, 90% Percoll (Pharmacia) diluted with m-BWW (2 ml) was charged, and 47% Percoll (Pharmacia) diluted with m-BWW (2 ml) and the human sperm (1 ml) were layered thereon in this order. On centrifugation at 800 xg for 30 minutes, mature sperm having good motility were precipitated. The precipiated sperm were collected by a micropipette (Gilson, "Pipetman p-1000" ®), washed with m-BWW and combined with m-BWW (HSA concentration, 3.5%) (1 ml). After pre-incubation in 5% $CO_2$-containing air at 37° C. for 4 hours, the resultant sperm was subjected to test.

Preparation of hamster ova

To m-BWW (HSA concentration, 3.5%) (0.4 ml), 10 to 20 hamster ova were added, and human sperm were added thereto to make a concentration of $1 \times 10^6$ cells/ml. Three hours after the insemination, an ascitic fluid of the antibody was added to make a 1000 dilution, and the reaction was carried out in 5% $CO_2$-containing air for 15 minutes. The ova were washed with m-BWW, transferred to an FITC-labeled goat anti-mouse Ig-(A+M+G) solution (15 μl) and reacted at room temperature for 15 minutes. After washing with m-BWW of the ova, the sperm attached to the ova were observed by a fluorescence microscope.

Reactivity of MH61 with sperm on hamster ovum

TABLE 3

| Ascitic fluid (1/1000 dilution) | No. of experiment | No. of ova examined | Penetrated ova (%) | Fertilization index (mean number of penetrated sperm/ova) | No. of sperm bound/ova |
|---|---|---|---|---|---|
| P3U1 | 6 | 49 | 75.4 ± 7.0 | 1.91 ± 0.42 | 11.4 ± 2.50 |
| DE | 4 | 30 | 0 | 0 | 0.26 ± 0.12** |
| MH61 | 5 | 41 | 22.8 ± 6.0*** | 0.29 ± 0.10** | 3.06 ± 1.26* |

Note: Significantly different from control:
*$p < 0.05$;
**$p < 0.01$;
***$p < 0.001$.

MH⊕showed significant control on the binding of human sperm to hamster ova and remarkable inhibition on the fusion of the sperm to the ova. Thus, it was revealed that the antibody participates in the fertilization. DE did not produce any significant difference In the sperm suspension, there were observed materials not reactive to the antibody MH61 or shining at the middle portion. However, almost all the sperm attached onto the hamster ovum were stained at the whole of the head portion.

Taking this observation and said report by Tulbot et al into consideration, it may be said that the antibody MH61 can specifically recognize the fertilizable sperm.

EXAMPLE 5

Preparation of test beads:
IgG conjugation binding to beads (1) Activation of beads (tosylation with p-toluenesulfonyl chloride)

1) An appropriate amount of non-diluted Dinabeads M-450 ® (uncoated) (30 mg/ml) was added to dry acetone and continuously washed according to the following steps:

| Step 1: | water/acetone = 7/3 (10 ml) |
| Step 2: | water/acetone = 6/4 (10 ml) |
| Step 3: | water/acetone = 2/8 (10 ml) |
| Step 4–6: | water/acetone = 0/10 (10 ml) |
| Step 7: | resuspended in acetone |

In each step, the beads were collected by the use of a magnet (1 minute), and the supernatant was discarded. Into a test tube, the water/acetone mixture in each step was charged, and the beads were suspended for 5 minutes therein.

2) Pyridine and p-toluenesulfonyl chloride were added to non-diluted Dinabeads M-450 (uncoated) respectively in amounts of 0.75 mmol and 0.3 mmol per 1 ml of said beads.

3) Incubation was carried out at room temperature for 20 hours while stirring.

4) The beads were collected by the use of a magnet and resuspended in acetone. Again, the beads were collected and washed with acetone three times.

5) The beads were treated in the order of Steps 3, 2 and 1 under the above 1) and returned to water.

6) The beads were collected, the supernatant was discarded and said beads were again resuspended in 1 mM HCl (10 ml).

The activated beads prepared as above are stable over a period of 12 months when stored in 1 mM HCl at 4° C.

Still, the activated beads as prepared above are per se marketed as a commercial product under the tradename "14003/14004 Dinabeads M-450 (tosyl-activated) ®".

(2) Conjugated binding to beads 1) 1 mM HCl suspension of the activated beads was washed with sterile distilled water.

2) Depending on the need, simple agitation was made so as to make a uniform suspension of the activated beads.

3) The purified antibody was dissolved in 0.2M borate buffer (pH, 9.5) to make a concentration of 150 μg/ml.

4) An equal volume of said suspension of the activated beads was added to said IgG solution (anti-body/beads-75 μg/15 mg).

5) Incubation was carried out at 22° C. for 24 hours while stirring slowly.

6) The beads were collected by the use of a magnet, and the supernatant was discarded.

7) The collected beads were washed in the following procedure: washing with 0.1M PBS (5 ml) for 10 minutes; washing with 0.1% Tween 20-containing 1M ethanolamine-HCl (pH, 9.5) (5 ml) for 2 hours (Tween 20 was added to the buffer immediately before the use); washed with 0.05M Tris (pH, 7.5) (5 ml) containing 0.1M NaCl, 0.1% BSA, 0.01% mertrhiolate and 0.1% Tween 20 for 12 hours; washed with 0.05M Tris (pH, 7.5) (5 ml) containing 0.1M NaCl, 0.1% BSA and 0.01% mertrhiolate for 2 hours.

8) The beads were collected by the use of a magnet, the supernatant was discarded and said beads were resuspended in PBS/BSA to make a desired concentration or a concentration of about $4 \times 10^8$ beads/ml (30 mg/ml). The thus obtained IgG-labeled beads are stable over a period of at least 6 months on the storage at 4° C. As the buffer for storage, 0.05M Tris containing 0.1M NaCl and 0.1% BSA was used.

Purification of monoclonal antibody

Saturated ammonium sulfate solution was added to an ascitic fluid to make a final concentration of 20%, and the resultant mixture was allowed to stand for 1 hour (4° C.). After centrifugation at 10,000xg for 15 minutes, the precipitate was discarded, and the supernatant was combined with saturated ammonium sulfate to make a final concentration of 40% (4° C.) and allowed to stand for 1 hour. After centrifugation at 10,000xg for 15 minutes, the supernatant was discarded, and the precipitate was dissolved in a solution of an ascitic fluid in a 2 fold volume of a buffer for protein A column adsorption (PIERCE Inc.). After centrifugation at 10,000xg under 4° C. for 15 minutes, the supernatant was collected and subjected to Protein A affinity chromatography, whereby about 3 to 4 mg of IgG per 1 ml ascitic fluid was obtained. The eluate was desalted by passing through a column of G25 and dialysing and freeze-dried to obtain the monoclonal antibody in a purified state.

Pre-treatment of beads with skim milk

A suspension of Dinabeads M-450 sheep-anti-mouse $IgG_1(Fc)$ ($4 \times 10^8$/ml) was agitated well to make a good suspending date, followed by centrifugation at 1000xg for 5 minutes. The supernatant was discarded, and the collected beads were suspended in an equal amount of 5% skim milk-containing PBS (prepared by adding skim milk to PBS to make a concentration of 5%, dissolving the skim milk at 60° C. for 1 hour and freeze-drying the resultant solution at $-20°$ C.) (about 2 ml), followed by shaking at 37° C. for 1 hour. The resulting mixture was centrifuged at 1,000xg for 5 minutes, washed with PBS three times and diluted with PBS to make a concentration of about $4 \times 10^8$/ml.

Preparation of test beads

To pre-treated beads (50 μl), an equal amount of the antibody MH61 (ascitic fluid) antibody was added, followed by shaking at 37° C. for 1 hour to make the antibody bound to the beads. After addition of PBS(−) (1 ml), centrifugation was carried out at 1,000xg at 4° C. for 5 minutes. The precipitate was washed two times with PBS(−). The thus obtained MH61 beads were suspended in PBS(−) containing 5% bovine newborn serum to make a concentration of $4 \times 10^8$/ml. On the use, this dilution was further diluted with m-BWW to make a concentration of $3 \times 10^6$/ml. The beads may be stored at 4° C. but should be consumed within one week.

EXAMPLE 6

Test method

The following articles and materials were prepared:
Sterilized tube (a) (50 ml, Sumitomo Bakelyte) for charging sperm therein.
Sterilized tube (b) (15 ml, Sumitomo Bakelyte) for measuring sperm therein.

Glass test tube (c) (12.5 mm in diameter, 10 ml) for sperm release.

Glass centrifugal tube (d) (10 ml) for sperm centrifugation.

Glass test tube (e) (10 ml) for beads test

Test tube support

Pipetman (p-1000, P-200, P-20)

Centrifuge (1000xg)

Microscope (x400) for observation

MH61 beads ($3 \times 10^6$ ml, in m-BWW)

m-BWW having the composition as shown in Table 4.

TABLE 4

| Component | g/l | mM |
|---|---|---|
| NaCl | 4.910 | 84.00 |
| KCl | 0.356 | 4.78 |
| $CaCl_2.2H_2O$ | 0.251 | 1.71 |
| $KH_2PO_4$ | 0.162 | 1.19 |
| $MgSO_4.7H_2O$ | 0.294 | 1.19 |
| Sodium pyruvate | 0.028 | 0.25 |
| Sodium lactate*[1] | (2.416) | 21.58 |
| Glucose | 1.000 | 5.56 |
| Phenol rod (10 mg/ml) | 400 μl | |
| Antibiotic*[2] | 10 ml | |
| $NaHCO_3$ | 3,000 | 35.71 |
| Human serum albumin*[3] | 3,000 (for swim up, wash) | |
| | 35,000 (for incubation) | |

Note:
*[1]DL-lactic acid; 60% syrup (Nakarai)
*[2]5000 IU/ml K-penicillin G and 5 mg/ml streptomycin sulfate in distilled water, stored frozen until use
*[3]Fraction V powder (Sigma Chem.)

In the above composition, a solution comprising the materials except $NaHCO_3$ and human serum albumin (each 40–50 ml) was admitted in a vessel and freeze-dried as a stock solution for storage. One day before the use for test, the freeze-dried product was returned to room temperature, combined with $NaHCO_3$ and human serum albumin, sterilizied by filtration and equilibrated with 5% $CO_2$ at 37° C. overnight.

Preparation of sperm suspension

Human adult sperm as ejaculated and comprising spermatozoa and fluids from the prostate gland, the seminal vesicle, etc. were collected in sterilized test tubes and allowed to stand at 37° C. for 30 to 60 minutes for liquefaction.

Four sterilized test tubes (c) were allowed to stand at 30° C., m-BWW (0.3% HSA) was charged into each of the test tubes, and the liquefied sperm (0.5 ml) was introduced therein gradually. After sealing with an aluminum cap, each test tube was allowed to stand in 5% $CO_2$-containing air at 37° C. for 60 minutes. Sperm having good motility were released into m-BWW as the upper layer, and such upper layer (about 1.5 ml) was transferred to a test tube for centrifugation (d) and centrifuged at 500xg under room temperature for 5 minutes. The supernatant was discarded, the precipitate was suspended in m-BWW (0.3% HSA), and centrifugation was made. This operation was repeated once again. The precipitate after the second operation was suspended in m-BWW (3.5% HSA) (1 ml), and 10 μl of this suspension was sampled, placed on a blood cell counting plate and subjected to determination of the number of sperm. Depending upon the number of sperm, centrifugation was carried out one more time, and m-BWB (3.5% HSA) was added thereto to make a concentration of $4 \times 10^6$ cells/ml. A part of the thus prepared sperm suspension was used for beads test.

Fertilizability acquisition of sperm

A human sperm suspension in m-BWW (3.5% HSA) having a concentration of $4 \times 10^6$ cells/ml was preincubated in 5% $CO_2$-containing air at 37° C. to obtain fertilizability.

The time for fertilizability acquisition is varied with each person and each solution, and a general rule thereon is hardly determined. Most male persons acquire, however, fertilizability within 24 hours so that the 24 hour beads test may be carried out after 24 hours.

Test

A sperm suspension to be incubated with the beads are desired to have a concentration of $4 \times 10^6$ cells/ml, because lower concentration would result in low reaction probability. The sperm suspension was combined with 10 μl of beads ($3 \times 10^6$ beads/ml) and allowed to stand in 5% $CO_2$-containing air for 1 hour. During this procedure, shaking should be avoided because the beads may attach to the test tube wall and their recovery is made difficult.

To the resulting suspension, an earth metal magnet was brought close so that the beads were collected within 1 to 2 minutes. While the magnet was retained in such state, the supernatant was eliminated by the use of a pipette. m-BWW (0.3% HSA) (500 μl) was added thereto, and the supernatant was again eliminated with retention of the pipette. This operation was repeated one more time. The recovered beads were placed on a slide glass and subjected to microscopic observation. The number of the beads to which sperm attached among 100 beads as observed was taken as the evaluation (i.e. index at beads test).

Results

The results as obtained are shown in Table 5.

TABLE 5

| Doner | Index at beads test |
|---|---|
| | (0 Hour later) |
| A | 1 |
| B | 0 |
| C | 4 |
| D | 3 |
| | (24 Hours later) |
| A | 49 |
| B | 55 |
| C | 39 |
| D | 68 |

What is claimed is:

1. A monoclonal antibody MH61 which shows a specific binding property to an antigenic site appearing on human sperm after the sperm acrosome reaction but does not bind to human sperm before the sperm acrosome reaction.

2. The antibody according to claim 1, which is produced by hybridoma MH61 having accession number FERM BP-2257.

3. A hybridoma MH61 having accession number FERM BP-2257.

4. A method for evaluation of sperm binding to monoclonal antibody MH61, which comprises the steps of admixing a sample of sperm collected from a male human person with test beads carrying a monoclonal antibody MH61 on their surfaces, incubating the resultant mixture, collecting the test beads and determining the number of the test beads with sperm attached thereto.

* * * * *